United States Patent
Ertl et al.

(10) Patent No.: US 10,113,192 B2
(45) Date of Patent: Oct. 30, 2018

(54) METHOD FOR PRODUCING FRUCTOSE

(71) Applicant: ANNIKKI GMBH, Graz (AT)

(72) Inventors: Ortwin Ertl, Vasoldsberg (AT); Marta Sut, Graz (AT); Martina Brandner, Grambach (AT)

(73) Assignee: ANNIKKI GMBH, Graz (AT)

( * ) Notice: Subject to any disclaimer, the term of this patent is extended or adjusted under 35 U.S.C. 154(b) by 139 days.

(21) Appl. No.: 14/763,678

(22) PCT Filed: Feb. 5, 2014

(86) PCT No.: PCT/EP2014/052230
§ 371 (c)(1),
(2) Date: Jul. 27, 2015

(87) PCT Pub. No.: WO2014/122167
PCT Pub. Date: Aug. 14, 2014

(65) Prior Publication Data
US 2015/0353978 A1    Dec. 10, 2015

(30) Foreign Application Priority Data
Feb. 6, 2013  (AT) .............................. A 50091/2013

(51) Int. Cl.
*C12P 19/02*   (2006.01)
(52) U.S. Cl.
CPC ....... *C12P 19/02* (2013.01); *C12Y 101/01307* (2013.01); *C12Y 101/0301* (2013.01)
(58) Field of Classification Search
None
See application file for complete search history.

(56) References Cited

U.S. PATENT DOCUMENTS

| | | | | |
|---|---|---|---|---|
| 4,246,347 A | * | 1/1981 | Neidleman | C07C 29/10 435/105 |
| 4,321,324 A | | 3/1982 | Maselli et al. | |
| 5,225,339 A | * | 7/1993 | Wong | C07F 7/0818 435/122 |
| 7,939,681 B2 | * | 5/2011 | Zhao | C07D 307/46 549/488 |

FOREIGN PATENT DOCUMENTS

| | | |
|---|---|---|
| EP | 0028136 | 5/1981 |
| EP | 0098533 | 1/1984 |
| EP | 1048672 | 11/2000 |
| WO | WO8103666 | 12/1981 |
| WO | WO2013117584 | 8/2013 |

OTHER PUBLICATIONS

Hers, "Le Mecanisme de la Formation Due Fructose Seminal et du Fructose Foetal", 37 (1960) 127-138.
Neuhauser et al: "NAD(P)H-dependent aldose reductase from the xylose-assimilating yeast *Candida tenuis*: Isolation, characterization and biochemical properties of the enzyme", Biochemical Journal, Bd. 326, Nr. 3, 1997, p. 683-692, XP002724842, cited in the application.
Nidetzky et al: "Transient-state and steady-state kinetic studies of the mechanism of NADH-dependent aldehyde reduction catalyzed by xylose reductase from the yeast *Candida tenuis*", Biochemistry, Bd. 40, Nr. 34, 28, 2001, p. 10371-10381, XP002724843.
Schroer et al: "Metabolomics for biotransformations: Intracellular redox cofactor analysis and enzyme kinetics offer insight into whole cell processes", Biotechnology and Bioengineering,Bd. 104, Nr. 2, 1. Oct. 2009 (Oct. 1, 2009), p. 251-260, XP055119764.
International Preliminary Report on Patentability for PCT App. No. PCT/EP2014/052230 dated Aug. 11, 2015.

* cited by examiner

*Primary Examiner* — Vera Afremova
(74) *Attorney, Agent, or Firm* — Workman Nydegger

(57) ABSTRACT

A method for the enzymatic production of D-fructose from D-glucose in a one-pot synthesis, wherein D-glucose is oxidized enzymatically to D-glucosone and D-glucosone is reduced enzymatically to D-fructose and the use of the D-fructose produced in this way for the production of furan derivatives.

14 Claims, No Drawings

METHOD FOR PRODUCING FRUCTOSE

The present invention relates to a method for producing D-fructose from D-glucose.

For the industrial manufacture of D-fructose, a method in two steps has so far been used conventionally, wherein D-glucose is produced by hydrolysis of polysaccharides such as, e.g., starch and, subsequently, the isomerization of the D-glucose obtained in this manner into D-fructose is carried out. Through isomerization of D-glucose, 42% D-fructose, 50% D-glucose and about 8% residual polysaccharides can be obtained. This entails the problem that the isolation of pure D-fructose from this mixture requires the application of elaborate and costly purification techniques.

An alternative to the production of D-fructose by isomerization of D-glucose is a method in which D-glucose is converted into D-fructose in an enzymatic step and a chemical step.

On the whole, a large number of different methods for producing D-fructose from D-glucose are known.

For example, a reduction of D-glucosone to D-fructose is known, which, in most cases, has been conducted in a chemical way, as described, for instance, in EP1048672. In said method, the D-fructose is produced through catalytic hydrogenation of a glucosone solution with a high dry matter content, with specific pressure and temperature conditions being employed.

In U.S. Pat. No. 4,321,324, the production of D-glucosone from D-glucose in an enzymatic step is described, wherein D-glucose is oxidized to D-glucosone via a pyranose-2-oxidase and the nascent hydrogen peroxide is separated through a semi-permeable membrane.

The reduction of D-glucosone to D-fructose in an enzymatic way by means of a reductase has been recommended, for example, in the book "Microbial Transformation of non-steroid cyclic compounds" by Kieslich, Georg Thieme Publishers, Stuttgart 1976, and in Biochem J. 1997 Sep. 15; 326 683-92, it has been described that a xylose reductase from *Candida tenuis* is able to reduce D-glucosone to D-fructose.

The production of D-fructose via isomerization of D-glucose in two steps (enzymatic and chemical) has been described, for example, in U.S. Pat. No. 4,246,347. According to the method described therein, D-glucose was initially converted enzymatically into D-glucosone, using a pyranose-2-oxidase. The hydrogen peroxide forming in the process was separated and reused or was degraded by a catalase. In a second step, D-glucosone which had formed was converted into D-fructose by hydrogenation. In said process, 2% glucose was used, and the two steps were carried out separately. The problems associated with the methods are a high pressure and high temperatures as well as low concentrations of the substrates used.

Known methods for the production/isomerization of D-fructose from D-glucose usually have different drawbacks. For example, an efficient conversion of the substrate at a high selectivity is, in most cases, possible only if high pressures and temperatures are applied, and the formation of contaminating by-products, which are difficult to separate, cannot easily be avoided.

Surprisingly, a method has now been found which enables an efficient conversion of the substrate at a high selectivity and without the use of high pressures and temperatures, wherein the formation of contaminating by-products can largely be avoided so that the separation of the substrate from the product is not necessary and the application of elaborate and costly purification techniques may be omitted.

In one aspect, the present invention provides a method for producing D-fructose from D-glucose, which is characterized in that, in a one-pot synthesis,
a) D-glucose is oxidized enzymatically to D-glucosone, and
b) D-glucosone is reduced enzymatically to D-fructose.

A method provided by the present invention is referred to herein also as the method according to/of the present invention.

Thus, the present invention relates to a method for producing D-fructose from D-glucose in a one-pot synthesis in two enzymatic steps:

An enzymatic oxidation of D-glucose to D-glucosone, followed by an enzymatic reduction of D-glucosone to D-fructose, which proceeds according to the following Reaction Scheme 1:

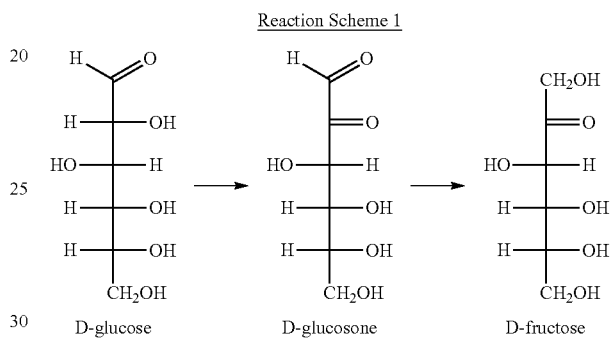

Reaction Scheme 1

A method according to the present invention provides a new enzymatic possibility of producing D-fructose without the need of separating and purifying residual D-glucose. Compared to currently employed techniques, the present invention thereby represents a substantial improvement of the methods for producing D-fructose from D-glucose. In contrast to existing methods, compounds are both enzymatically oxidized and enzymatically reduced without having to isolate an intermediate. At the same time, significantly higher substrate concentrations can be used and, also, a higher turnover can be achieved, in comparison to what was possible in previously employed methods.

Suitable sources of D-glucose in a method according to the present invention are, for example, enzymatic or non-enzymatic hydrolysates of starch, in particular corn starch, enzymatic or non-enzymatic hydrolysates of saccharose or enzymatic or non-enzymatic hydrolysates of cellulose. Cellulose which can be used in a method according to the present invention may be obtained, for example, from a biomass, preferably from a lignocellulosic biomass such as, e.g., wood, straw such as wheat straw, corn straw, bagasse, sisal, energy grasses. For example, amylases may be used for the enzymatic hydrolysis of corn starch. For example, invertases are suitable for the enzymatic cleavage of saccharose. For example, cellulases may be used for the enzymatic cleavage of cellulose. An acid-catalyzed cleavage, for example, is suitable for the non-enzymatic cleavage of said multiple sugars.

A method according to the present invention is preferably carried out in an aqueous system. A buffer (system) may also be added to the aqueous system. Suitable buffer (systems) are known and include conventional buffer (systems), for example, acetate, potassium phosphate, Tris-HCl and glycine buffers. A buffer used in a method according to the present invention preferably has a pH value of from 5 to 10.5, preferably from 6 to 9.5. For stabilizing the enzymes, stabilizers, for example, common stabilizers such as, e.g., ions, e.g. $Mg^{2+}$, or other additives, for example, common additives such as, e.g., glycerol, may be added to the aqueous system.

In a method according to the present invention, oxygen is required for the oxidation of D-glucose to the D-glucosone. Said oxygen can be introduced as usual and can be made available, for example, through contact with ambient air or an increased oxygen supply, for example by compressed air or the injection of pure oxygen.

A method according to the present invention is carried out at suitable temperatures which may depend, for example, on the enzymes used. Suitable temperatures include 10° C. to 70° C., preferably 20° C. to 50° C., e.g., 20° C. to 45° C.

A method in which the oxidation reaction and the reduction reaction are carried out in the same reaction batch without intermediates being isolated, in particular wherein two enzymatic redox reactions involved in the product formation and an enzymatic system for cofactor regeneration are performed in one reaction batch without isolating an intermediate, is herein referred to as a "one-pot synthesis". In the process, either all the involved enzymes can be added simultaneously, or at first a portion of the enzymes is added, for example, the enzyme(s) for step a) and, with a time delay, another portion of the enzymes, for example, the enzyme(s) for step b). Before the second portion of the enzymes is added, the enzymes which are already present in the reaction batch may, for example, be inactivated, for instance, by a conventional method such as, e.g., an increase in the temperature, for example, to 65° C. for 10 min.

In a particular aspect, a method according to the present invention is characterized in that the method takes place without intermediates being isolated.

The oxidation of D-glucose to D-glucosone in a method according to the present invention occurs enzymatically, namely through enzymatic catalysis, and may be carried out according to a known method. The oxidation is preferably effected through catalysis with an oxidase, in particular with a pyranose-2-oxidase.

Suitable oxidases are known and include common oxidases such as, for example, pyranose-2-oxidases. Pyranose-2-oxidases are obtainable, for example, from *Coriolus* sp., *Aspergillus* sp. or *Polyporus obtusus*.

A particular embodiment of the method according to the present invention is characterized in that the oxidation of D-glucose to D-glucosone is catalyzed by a pyranose-2-oxidase.

During the reaction of the pyranose-2-oxidase, $H_2O_2$ emerges which is removed from the reaction mixture. The removal of $H_2O_2$ may occur according to conventional methods and preferably occurs enzymatically, for example, with the aid of a catalase. For example, a catalase is added to the reaction mixture.

A particular embodiment of the method according to the present invention is characterized in that nascent $H_2O_2$ is removed with the aid of a catalase.

Suitable catalases are known and are obtainable, for example, from *Aspergillus* sp., *Corynebacterium glutamicum* or from bovine liver.

The enzymatic reduction of D-glucosone to D-fructose in a method according to the present invention may occur according to a suitable method, for example, according to a conventional method, or as herein described. Suitable, e.g., common enzymes which are suitable for the reduction of substrates may be used as enzymes for the reduction. Suitable enzymes comprise, for example, reductases, in particular xylose reductases.

Suitable xylose reductases are known and are obtainable, for example, from *Candida tropicalis, Candida parapsilosis* or *Debariomyces hansenii*.

A particular embodiment of the method according to the present invention is characterized in that a xylose reductase is used for the reduction of D-glucosone to D-fructose.

In a method according to the present invention, a redox cofactor, in particular $NAD(P)H/NAD(P)^+$, is preferably used, in particular NAD(P)H is used as a redox cofactor for the reduction of the D-glucosone to the D-fructose. In this connection, NAD+ denotes the oxidized form and NADH denotes the reduced form of nicotinamide adenine dinucleotide, whereas NADP denotes the oxidized form and NADPH denotes the reduced form of nicotinamide adenine dinucleotide phosphate. By using a cell lysate of the microorganism expressing the involved enzymes, for example, *E. coli* such as, e.g., *E. coli* BL21 (DE 3), in which the required NAD(P) is contained, the expensive addition of said cofactor can be omitted in some circumstances. If the redox cofactors $NAD(P)^+$ and/or NAD(P)H are added during the conversion of D-glucose into D-fructose, the added concentration usually ranges from 0.001 mM to 10 mM, preferably from 0.01 mM to 1 mM, in a method according to the present invention.

A particular embodiment of the method according to the present invention is characterized in that, in particular during the reduction of D-glucosone, redox cofactors, in particular NAD(P)H, are used, in particular that the enzyme used in step b) is NADP(H)-dependent.

Redox cofactors can be regenerated by a suitable cofactor regeneration system, that is, they can be subjected to recycling, wherein the cofactors are reconverted into the form as originally employed.

A particular embodiment of the method according to the present invention is characterized in that redox cofactors which are used are subjected to recycling, in particular by a suitable cofactor regeneration system.

The regeneration of redox cofactors generally requires the presence of a suitable cosubstrate which is used up during the regeneration of the redox cofactors. Cosubstrates which can be used, for example, if the cofactors $NAD(P)H/NAD(P)^+$ are used include, for instance, alcohols such as, e.g., isopropyl alcohol (2-propanol, IPA), lactic acid and salts thereof, pyruvic acid and salts thereof, oxygen, hydrogen and/or formic acid and salts thereof.

In a particular aspect, a method of the present invention is characterized in that the redox cofactor is regenerated if the cofactors $NAD(P)H/NAD(P)^+$ are used, in particular for the reduction of D-glucosone, consuming a cosubstrate in particular selected from an alcohol, lactic acid and salts thereof, pyruvic acid and salts thereof, oxygen, hydrogen and/or formic acid and salts thereof.

A particular embodiment of a method according to the present invention is characterized in that cosubstrates are used for the regeneration of the redox cofactors, in particular for the reduction of D-glucosone to the D-fructose.

For the regeneration of redox cofactors, a redox enzyme is used. Redox enzymes which come into consideration as redox cofactors if $NAD(P)H/NAD(P)^+$ is used include, for example, dehydrogenases, e.g., alcohol dehydrogenases, lactate dehydrogenases, formate dehydrogenases, preferably alcohol dehydrogenases. Suitable alcohol dehydrogenases are known and include, for example, an alcohol dehydrogenase obtainable from *Lactobacillus kefir*.

In a further particular embodiment of the method according to the present invention, the redox cofactor is regenerated by a redox enzyme, in particular by an alcohol dehydrogenase.

In a method according to the present invention, enzymes may be used as such, optionally in the form of cell lysates, optionally as recombinantly overexpressed proteins, for example, as proteins recombinantly overexpressed in *E. coli*, wherein the appropriate cell lysates can preferably be used without any further purification. Depending on the enzyme to be produced, other microorganisms may also be used for the expression, for example, microorganisms known to the skilled artisan. In a method according to the present invention, solid components of the respective microorganisms can either be separated or used in the reaction, too (e.g., whole-cell biokatalysts). Culture supernatants or lysates from microorganisms which already display sufficient enzyme activities without recombinant DNA technology may also be used. Thereby, the enzyme unit 1 U corresponds to the enzyme amount which is required for reacting 1 μmol of substrate per min.

In a method according to the present invention, both one or several enzymes and one or several redox cofactors may be used in the conversion of D-glucose into D-fructose, either in a soluble form or immobilized on carriers (solids).

In a further aspect, a method according to the present invention is characterized in that it proceeds according to the following Reaction Scheme 2

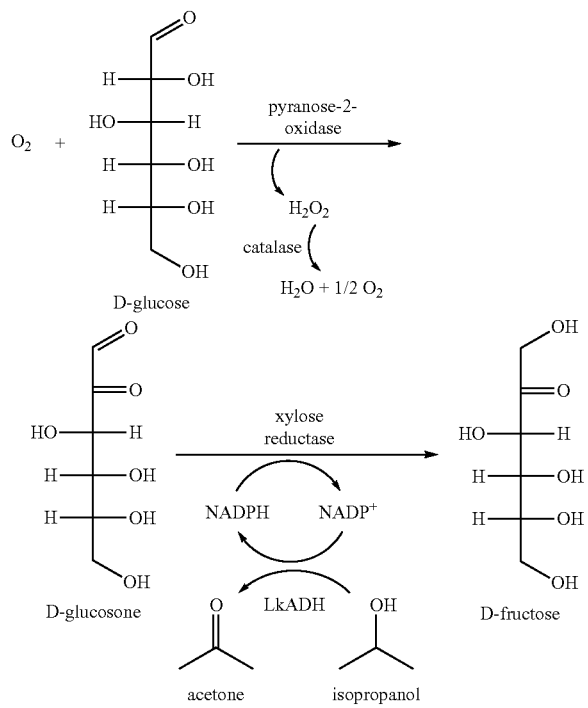

in which LkADH denotes an alcohol dehydrogenase, in particular an alcohol dehydrogenase from *Lactobacillus kefir*, which is NADP(H)-dependent.

D-Fructose, which has been obtained according to the present invention, can be isolated from the reaction mixture, for example, according to a conventional method, e.g., by means of crystallization.

In the chemical industry, D-fructose represents an important starting material for further processing. For example, it is known that D-fructose can be processed further to furan derivatives such as, e.g., hydroxymethylfurfural (HMF) of formula

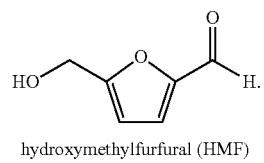

hydroxymethylfurfural (HMF)

Hydroxymethylfurfural is known to be a starting product for the production of 2,5-furandicarboxylic acid (FDCA) of formula

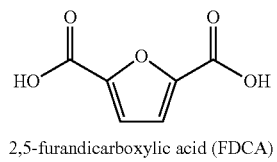 [SMILES: O=C(O)c1ccc(C(=O)O)o1]

2,5-furandicarboxylic acid (FDCA)

which is known to be suitable as a monomer for the production of polymers such as, for example, polyethylene furanoate (PEF). PEF can be used similarly to polyethylene terephthalate (PET), for example, for the production of hollow bodies, in particular bottles such as, e.g., beverage bottles, bottles for cosmetics or bottles for cleaning agents. If ethylene glycol from regenerative sources and FDCA, which is accessible from HMF produced in a method according to the present invention, are used simultaneously, PEF consisting completely of renewable raw materials can be obtained.

In a particular embodiment of the method according to the present invention, the produced fructose is converted further into furan derivatives such as, e.g., hydroxymethylfurfural (HMF) of formula

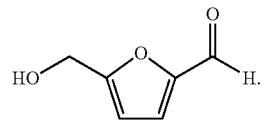

In the following examples, all temperature data are given in degrees Celsius (° C.). The enzyme unit "1 U" thereby corresponds to the enzyme amount which is required for reacting 1 μmol of substrate per min.

The following abbreviations are used:
h hour(s)
min minute(s)

EXAMPLE 1

Bioconversion of D-Glucose into D-Glucosone Via Pyranose Oxidase, Using Catalase for Removing the $H_2O_2$ Formed Thereby A 0.5 ml batch contains 2.5% (w/v) D-glucose and 1 U of pyranose-2-oxidase (Sigma Aldrich). For converting the $H_2O_2$ formed in this reaction, 50 U of catalase (Sigma Aldrich) is used which converts the nascent $H_2O_2$ into $H_2O+\frac{1}{2}O_2$. The reaction is carried out in a Tris-HCl buffer (50 mM, pH 7.0) at 30° C. under continuous shaking (850 rpm). An open system is used in order to achieve a sufficient supply of oxygen. After 48 h, 99% of the D-glucose had been converted into D-glucosone.

EXAMPLE 2

Bioconversion of D-Glucosone into D-Fructose Via Xylose Reductase, Using an Alcohol-Dehydrogenase Dependent Cofactor Regeneration System A 0.5 ml batch contains 2.5% (w/v) D-glucosone and 10 U of the recombinant xylose reductase from *Candida tropicalis* (overexpressed in *E. coli* BL21 (DE3)). For the regeneration of NADPH, 10 U of the recombinant alcohol dehydrogenase from *Lactobacillus kefir* (overexpressed in *E. coli* BL21 (DE3)) and initially 5% (w/v) 2-propanol are used. The reaction is carried out without addition of NADPH. The cofactor is provided by the cell extract of the *E. coli* BL21 (DE3) used for the expression of the xylose reductase and the alcohol dehydrogenase. The reaction is carried out in a Tris-HCl buffer (50 mM, pH 7.0) at 30° C. and under continuous shaking (850 rpm). An open system is used in order to enable the evaporation of acetone and to shift the reaction toward D-fructose. 2.5% (w/v) IPA is additionally dosed in after 6 h, 5% IPA (w/v) after 18 h and 2.5% (w/v) IPA after 24 h. After 48 h, ~90% of the D-glucosone had been converted into D-fructose.

EXAMPLE 3

Bioconversion of D-Glucose into D-Glucosone and Further into D-Fructose in a One-pot Synthesis (Two Consecutive Steps without the Intermediate being Isolated), Using an Alcohol-Dehydrogenase Dependent Cofactor Regeneration System A 0.5 ml batch contains 2.5% (w/v) D-glucose and 1 U of pyranose-2-oxidase (Sigma Aldrich). For converting the $H_2O_2$ formed in this reaction, 50 U of catalase is used which converts the nascent $H_2O_2$ into $H_2O+\frac{1}{2}O_2$. The reaction is carried out in a Tris-HCl buffer (50 mM, pH 7.0) at 30° C. under continuous shaking (850 rpm). Furthermore, an open system is used in order to achieve a sufficient supply of oxygen. After 24 h, the reaction mixture is heated to 65° C. for 10 minutes in order to inactivate the enzymes. Subsequently, 10 U of the recombinant xylose reductase from *Candida tropicalis* (overexpressed in *E. coli* BL21 (DE3)) is added to the reaction mixture. For the regeneration of NADPH, 10 U of the recombinant alcohol dehydrogenase from *Lactobacillus kefir* (overexpressed in *E. coli* BL21 (DE3)) and initially 5% (w/v) 2-propanol are used. The reaction is carried out without addition of NADPH. The cofactor is provided by the cell extract of the *E. coli* BL21 (DE3) used for the expression of the recombinant xylose reductase and the recombinant alcohol dehydrogenase. The reaction is carried out at 30° C. and under continuous shaking (850 rpm). An open system is used in order to enable the evaporation of acetone and to shift the reaction toward D-fructose. 2.5% (w/v) IPA is additionally dosed in after 6 h, 5% IPA (w/v) after 18 h and 2.5% (w/v) IPA after 24 h. After 48 h, 91% of the employed D-glucose had been converted into D-fructose.

The invention claimed is:

1. A method for producing D-fructose from D-glucose, comprising:
   a) enzymatically oxidizing D-glucose to D-glucosone in a reaction vessel, and
   b) enzymatically reducing the D-glucosone to D-fructose in reaction vessel,
   wherein a redox cofactor is used in step b) and the redox cofactor is recycled by a cofactor regeneration system comprising a redox enzyme
   wherein both enzymatic reaction of steps a) and b) are carried out in the reaction vessel and without the D-glucosone being isolated.

2. A method according to claim 1, wherein the enzymatic oxidation of D-glucose to D-glucosone is catalyzed by a pyranose-2-oxidase.

3. A method according to claim 2, wherein nascent $H_2O_2$ is removed with the aid of a catalase.

4. A method according to claim 1, wherein a xylose reductase is used for the enzymatic reduction of D-glucosone to D-fructose.

5. A method according to claim 1, wherein the redox cofactor comprises $NAD(P)H/NAD(P)^+$ and is used for the reduction of D-glucosone to D-fructose, and wherein the cofactor regeneration system includes consuming a cosubstrate.

6. A method according to any one of claims 1, 2, 3, 4, or 5, wherein the reactions proceed according to the following Reaction Scheme 2:

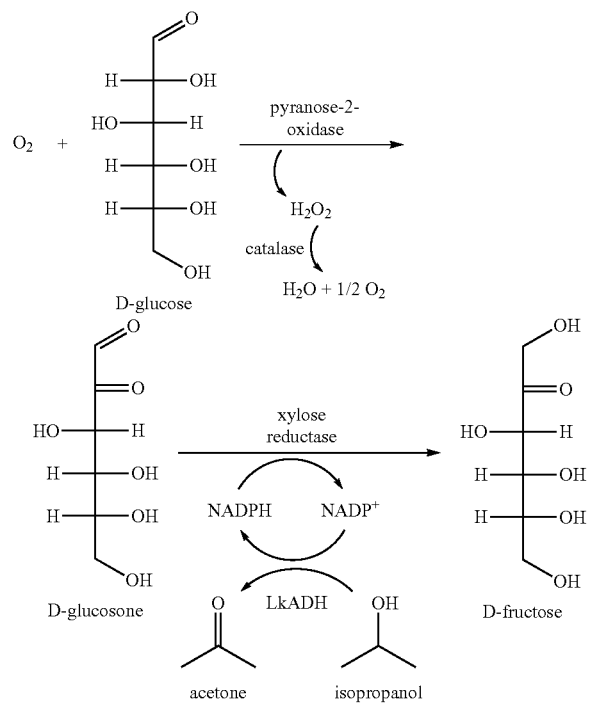

in which LkADH denotes an alcohol dehydrogenase which is NADP(H)-dependent.

7. A method according to claim 1, wherein the produced D-fructose is converted further into furan derivatives.

8. A method according to claim 1, wherein redox cofactor NAD(P)H is used.

9. A method according to claim 1, wherein redox cofactor NAD(P)H is used and step b) uses an enzyme that is NADP(H)-dependent.

10. A method according to claim 1, wherein the redox enzyme is an alcohol dehydrogenase.

11. A method according to claim 1, wherein the redox enzyme is an alcohol dehydrogenase from *Lactobacillus kefir*.

12. A method according to claim 5, wherein the cosubstrate is selected from an alcohol, lactic acid and salts thereof, pyruvic acid and salts thereof, oxygen, hydrogen and/or formic acid and salts thereof.

13. A method according to claim 1, wherein a redox enzyme regenerating the redox cofactor is different from an enzyme for enzymatically reducing D-glucosone to D-fructose.

14. A method for producing D-fructose from D-glucose, comprising:
  a) enzymatically oxidizing D-glucose to D-glucosone in a single reaction vessel, and
  b) without removing or isolating any materials involved in step a) from the single reaction vessel, enzymatically reducing the D-glucosone to D-fructose in the single reaction vessel.

* * * * *